US00PP21500P2

(12) United States Plant Patent
van Veen

(10) Patent No.: US PP21,500 P2
(45) Date of Patent: Nov. 16, 2010

(54) ***ASTILBE* PLANT NAMED 'MOULIN ROUGE'**
(50) Latin Name: ***Astilbe crispa*×*Astilbe japonica***
Varietal Denomination: Moulin Rouge

(76) Inventor: Wilhelmus Franciscus van Veen, Veenweg 12, 2432CA Noorden (NL)

( * ) Notice: Subject to any disclaimer, the term of this patent is extended or adjusted under 35 U.S.C. 154(b) by 0 days.

(21) Appl. No.: 12/462,524

(22) Filed: Aug. 5, 2009

(51) Int. Cl.
*A01H 5/00* (2006.01)

(52) U.S. Cl. ..... Plt./407

(58) Field of Classification Search ..... Plt./407

See application file for complete search history.

*Primary Examiner*—June Hwu
(74) *Attorney, Agent, or Firm*—C. A. Whealy

(57) ABSTRACT

A new and distinct cultivar of *Astilbe* plant named 'Moulin Rouge', characterized by its compact, upright and strong plant habit; strong and healthy foliage; freely and uniformly flowering habit; dark-colored leaves; red purple-colored flowers; and good garden performance.

2 Drawing Sheets

Botanical designation: *Astilbe crispa* ×*Astilbe japonica*.
Cultivar denomination: 'Moulin Rouge'.

BACKGROUND OF THE INVENTION

The present invention relates to a new and distinct cultivar of *Astilbe* plant, botanically known as *Astilbe crispa* ×*Astilbe japonica* and hereinafter referred to by the name 'Moulin Rouge'.

The new *Astilbe* plant is a product of a planned breeding program conducted by the Inventor in Noorden, The Netherlands. The objective of the breeding program was to create new compact *Astilbe* cultivars with attractive foliage and flower coloration.

The new *Astilbe* plant originated from a cross-pollination made by the Inventor in June, 2004 in Noorden, The Netherlands, of *Astilbe crispa* 'Perkeo', not patented, as the female, or seed, parent with *Astilbe japonica* 'Red Sentinel', not patented, as the male, or pollen, parent. The new *Astilbe* plant was discovered and selected by the Inventor as a single flowering plant within the progeny of the stated cross-pollination in a controlled greenhouse environment in Noorden, The Netherlands in June, 2005.

Asexual reproduction of the new *Astilbe* plant by divisions in a controlled environment in Noorden, The Netherlands since January, 2006, has shown that the unique features of this new *Astilbe* plant are stable and reproduced true to type in successive generations.

SUMMARY OF THE INVENTION

Plants of the new *Astilbe* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Moulin Rouge' . These characteristics in combination distinguish 'Moulin Rouge' as a new and distinct cultivar of *Astilbe:*

1. Compact, upright and strong plant habit.
2. Strong and healthy foliage.
3. Freely and uniformly flowering habit.

4. Dark-colored leaves.
5. Red purple-colored flowers.
6. Good garden performance.

Plants of the new *Astilbe* differ primarily from plants of the female parent,'Perkeo', primarily in flower color as plants of 'Perkeo' have purple-colored flowers.

Plants of the new *Astilbe* differ primarily from plants of the male parent, 'Red Sentinel', primarily in growth habit as plants of 'Red Sentinel' are taller than plants of the new *Astilbe.*

Plants of the new *Astilbe* can be compared to plants of *Astilbe crispa* 'Lilliput', not patented. In side-by-side comparisons conducted in Noorden, The Netherlands, plants of the new *Astilbe* differed primarily from plants of 'Lilliput' in flower color as plants of 'Lilliput' had pink-colored flowers.

BRIEF DESCRIPTION OF THE PHOTOGRAPHS

The accompanying colored photographs illustrate the overall appearance of the new *Astilbe* plant, showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet comprises a side perspective view of a typical flowering plant of 'Moulin Rouge' grown in a container.

The photograph at the top of the second sheet is a close-up view of typical inflorescences of 'Moulin Rouge'.

The photograph at the bottom of the second sheet is a close-up view of the upper surface of a typical leaf of 'Moulin Rouge'.

DETAILED BOTANICAL DESCRIPTION

The aforementioned photographs and following observations, measurements and values describe plants grown in containers in Noorden, The Netherlands, under commercial practice in during the summer in an outdoor nursery with day temperatures ranging from 12° C. to 32° C. and night temperatures ranging from 4° C. to 16° C. Plants were one year old when the photographs and description were taken. In the following description, color references are made to The Royal Horticultural Society Colour Chart, 2001 Edition, except where general terms of ordinary dictionary significance are used.

Botanical classification: *Astilbe crispa* ×*Astilbe japonica* 'Moulin Rouge'.

Parentage:

*Female, or seed, parent.*—*Astilbe crispa* 'Perkeo', not patented.

Male, or pollen, parent.—Astilbe japonica 'Red Sentinel', not patented.

Propagation:

*Type.*—By divisions.

*Time to initiate roots.*—About two weeks at 12° C. to 18° C.

*Time to produce a rooted young plant.*—About eight weeks at 15° C. to 30° C.

*Root description.*—Thin, fibrous; brown to black in color.

*Rooting habit.*—Moderately branching; dense.

Plant description:

*Plant form/habit.*—Herbaceous perennial; compact, upright and strong plant habit; roughly triangular; flowering stems and leaves basal; dense and bushy growth habit; low vigor; freely and uniformly flowering with numerous flowers on branched panicles.

*Growth rate.*—Moderate to slow; from divisions, about nine to ten weeks are required to produce fully-grown flowering plants.

*Plant height* (*soil level to top of foliar plane*).—About 7.1 cm.

*Plant height* (*soil level to top of inflorescences*).—About 28.6 cm.

*Plant width* (*spread*).—About 20.1 cm.

*Stem description.*—Length: About 4.8 cm. Diameter: About 1.3 cm. Internode length: About 4 mm. Strength: Strong. Texture: Pubescent. Color: Close to 144B.

Foliage description:

*Arrangement.*—Alternate; biternately compound.

*Leaf length* (*excluding petiole*).—About 11.9 cm.

*Leaf width.*—About 11 cm.

*Lateral leaflet length.*—About 2.6 cm.

*Lateral leaflet width.*—About 1.4 cm.

*Terminal leaflet length.*—About 4 cm.

*Terminal leaflet width.*—About 2.3 cm.

*Lateral and terminal leaflet shape.*—Ovate to narrowly ovate.

*Lateral and terminal leaflet apex.*—Acute.

*Lateral and terminal leaflet base.*—Rounded to cordate.

*Lateral and terminal leaflet margin.*—Biserrate.

*Lateral and terminal leaflet texture, upper surface.*—Smooth, glabrous.

*Lateral and terminal leaflet texture, lower surface.*—Sparsely pubescent; slightly rough.

*Lateral and terminal leaflet venation pattern.*—Pinnate.

*Lateral and terminal leaflet color.*—Developing leaves, upper surface: Close to 137A. Developing leaves, upper surface: Close to 147B. Fully expanded leaves, upper surface: Darker than between 139A and 147A; towards the margins, close to N186B; venation, close to 173B to 173C. Fully expanded leaves, lower surface: Close to 147A; venation, close to 178B to 178C.

*Leaf petiole length.*—About 2.2 cm.

*Leaf petiole diameter.*—About 4.5 mm.

*Leaflet petiole length.*—About 2 mm.

*Leaflet petiole width.*—About 1 mm.

*Leaf and leaflet petiole texture, upper and lower surfaces.*—Smooth, glabrous.

*Leaf and leaflet petiole color, upper surface.*—Close to 174A; at the nodes, close to 183B.

*Leaf and leaflet petiole color, lower surface.*—Close to 144B to 144C.

Flower description:

*Flower type/habit.*—Numerous single rotate flowers arrange on terminal branched panicles; flowers fact upright, outward or downward depending on position on the panicle; panicles triangular in shape; freely and uniformly flowering habit with about 1,000 flowers and flower buds per inflorescence.

*Fragrance.*—Faintly fragrant; sweet.

*Natural flowering season.*—Continuously flowering during the summer to late summer in The Netherlands.

*Postproduction longevity.*—Flowers last about ten days on the plant; flowers persistent.

*Flower buds.*—Height: About 1.6 mm. Diameter: About 1.2 mm. Shape: Broadly ovoid. Color: Close to 61B; towards the base, close to 146A.

*Inflorescence height.*—About 23.3 cm.

*Inflorescence diameter.*—About 14.3 cm.

*Flower diameter.*—About 6 mm.

*Flower depth.*—About 3.5 mm.

*Petals.*—Quantity per flower: Typically five in a single whorl. Length: About 3 mm. Lobe width: About 0.9 mm. Shape: Oblanceolate. Apex: Broadly acute. Margin: Entire. Texture, upper and lower surfaces: Smooth, glabrous Color: Developing petals, upper and lower surfaces: Close to 61B. Fully expanded petals, upper and lower surfaces: Close to 68A; towards the base, close to 68D; color becoming closer to 68D with development.

*Sepals.*—Quantity per flower: Typically five in a single whorl, fused towards the base; campanulate calyx. Length: About 1 mm. Width: About 0.8 mm. Shape: Ovate. Apex: Acute. Base: Cuneate, fused. Margin: Entire. Texture, upper and lower surfaces: Smooth, glabrous. Color: Developing sepals, upper and lower surfaces: Close to 60B; lower half and base, close to 145B to 145C. Fully developed sepals, upper and lower surfaces: Close to 60B; lower half and base, close to 145B to 145C.

*Peduncles.*—Length: About 22.8 cm. Diameter: About 3 mm. Angle: Erect to about 30° from vertical. Strength: Strong. Texture: Smooth, glabrous. Color: Close to 147A tinged with close to 183A to 183B.

*Pedicels.*—Length: About 0.7 mm. Diameter: About 0.5 mm. Angle: About 45° from vertical. Strength: Moderately strong. Texture: Smooth, glabrous. Color: Close to 147B tinged with close to 183B.

*Reproductive organs.*—Stamens: Quantity per flower: Typically ten; anthers basifixed. Filament length: About 2 mm. Anther shape: Ovate. Anther length: About 0.2 mm. Anther color: Close to 63C. Pollen amount: Scarce. Pollen color: Close to 155D. Pistils: Quantity per flower: Two, rudimentary. Pistil length: About 0.1 mm. Stigmas: Not present. Style length: About 0.1 mm. Style color: Close to 68A. Ovary color: Close to 160B to 160C.

*Seed/fruit.*—Seed and fruit development have not been observed.

Disease/pest resistance: Plants of the new *Astilbe* have not been noted to be resistant to pathogens and pests common to *Astilbe.*

Garden performance: Plants of the new *Astilbe* have been observed to have good garden performance and tolerate ram, wind and high temperatures of about 35° C. Plants of the new *Astilbe* have been observed to be hardy to USDA Zone 5.

It is claimed:

1. A new and distinct *Astilbe* plant named 'Moulin Rouge' as illustrated and described.

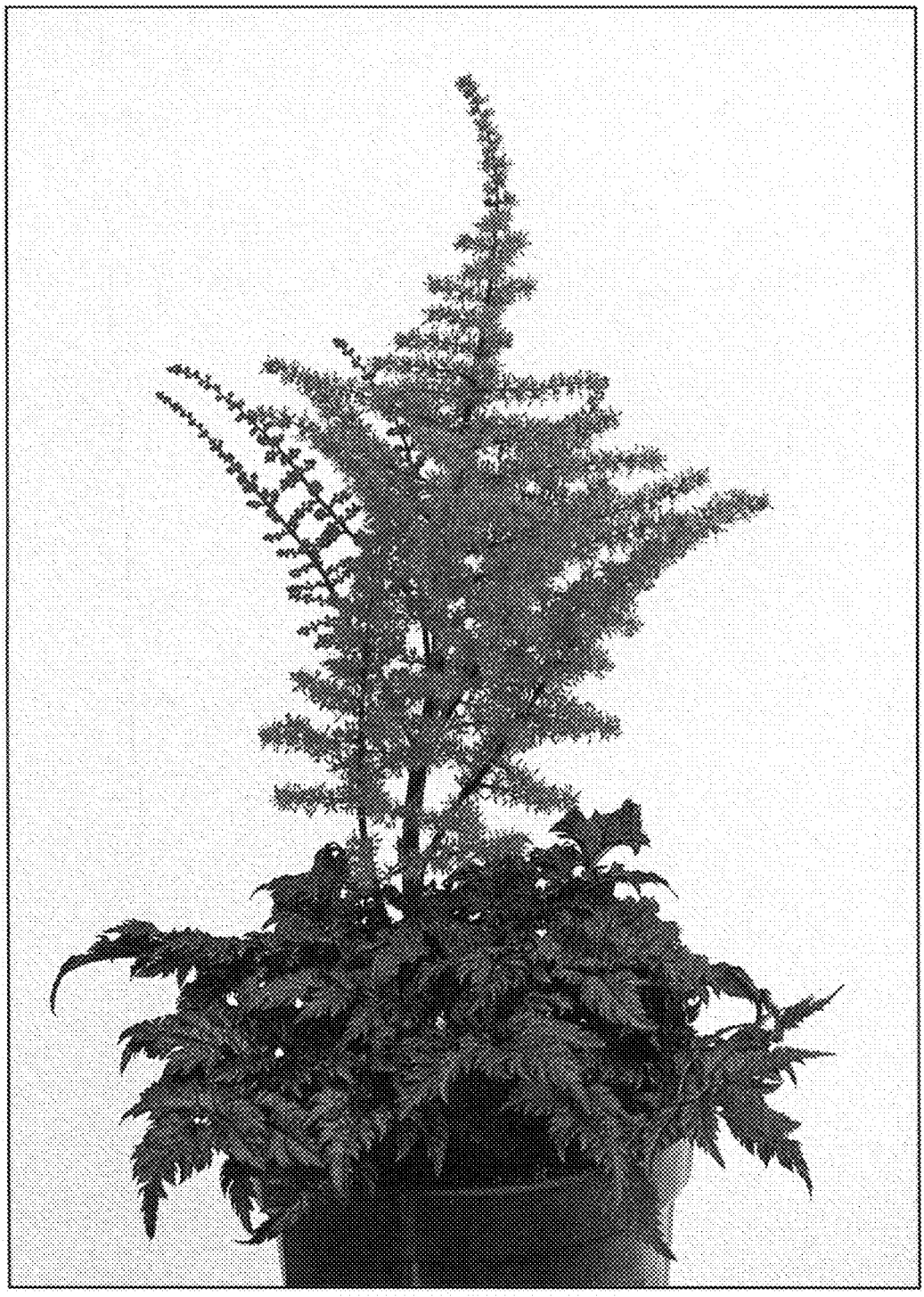

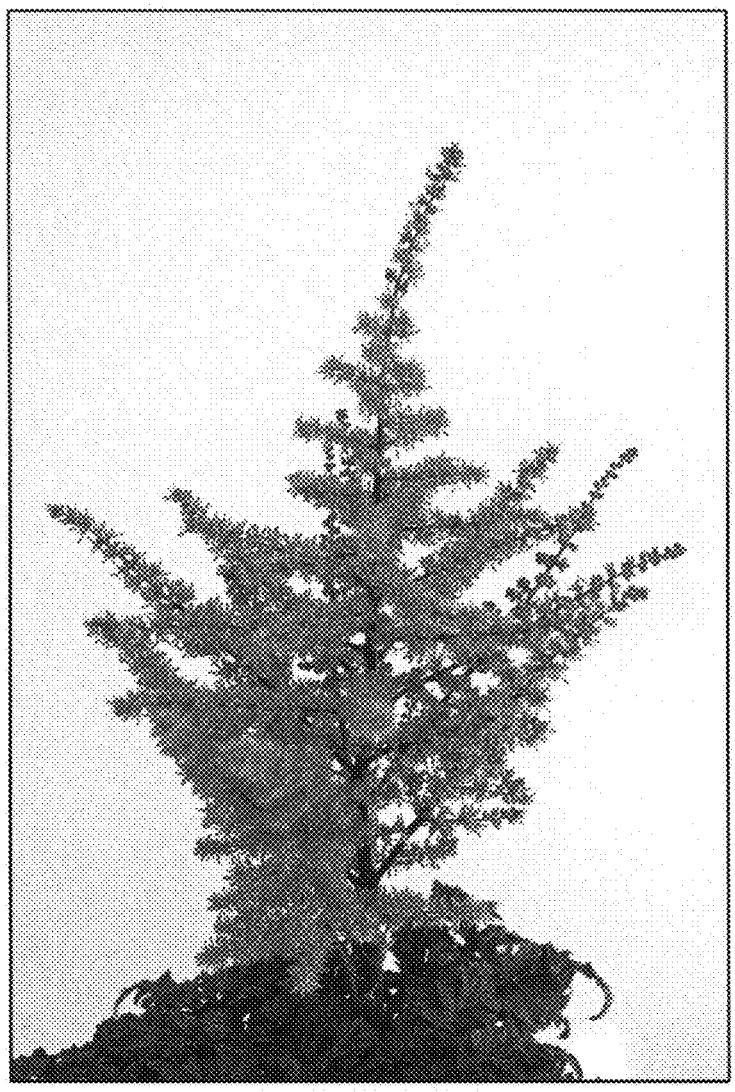
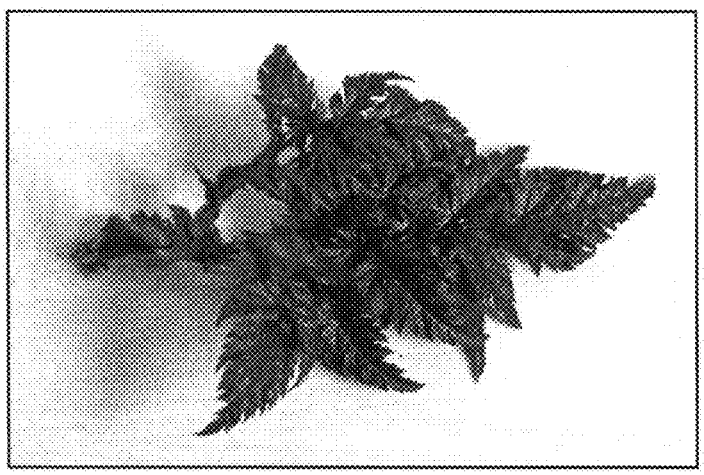

* * * * *